United States Patent [19]

Cobb

[11] Patent Number: 4,568,784

[45] Date of Patent: Feb. 4, 1986

[54] PREPARATION OF POLYMETHYLBENZENES

[75] Inventor: Raymond L. Cobb, Bartlesville, Okla.

[73] Assignee: Phillips Petroleum Company, Bartlesville, Okla.

[21] Appl. No.: 703,007

[22] Filed: Feb. 19, 1985

[51] Int. Cl.$^4$ .......................... C07C 2/64; C07C 2/66
[52] U.S. Cl. ..................................... 585/446; 585/467
[58] Field of Search ................ 568/804, 794; 585/446, 585/467

[56] References Cited

U.S. PATENT DOCUMENTS

| | | | |
|---|---|---|---|
| 3,463,824 | 8/1969 | Velling | 568/804 |
| 3,641,182 | 2/1972 | Box, Jr. et al. | 260/680 R |
| 3,674,706 | 7/1972 | Box, Jr. et al. | 252/412 |
| 3,737,466 | 6/1973 | Sharp et al. | 260/621 R |
| 3,869,524 | 3/1975 | Light et al. | 260/671 M |
| 3,994,982 | 11/1976 | Leach | 260/621 R |
| 4,085,150 | 4/1978 | Smith | 568/804 |
| 4,126,749 | 11/1978 | Leach | 568/804 |

FOREIGN PATENT DOCUMENTS

| | | | |
|---|---|---|---|
| 7704056 | 10/1977 | Netherlands | 568/804 |
| 1398560 | 6/1975 | United Kingdom | 568/804 |

OTHER PUBLICATIONS

Organic Syntheses, Collective vol. 4, John Wiley and Sons, Inc., New York, N.Y., pp. 520 and 521.

*Primary Examiner*—Werren B. Lone
*Attorney, Agent, or Firm*—K. K. Brandes

[57] ABSTRACT

A process is provided for preparing polymethylbenzenes by simultaneously contacting (a) a phenolic compound, preferably phenol, with (b) a methylating agent, preferably methanol, in the presence of (c) zinc aluminate as catalyst, under such conditions as will result in the at least partial conversion of the reactants to either pentamethylbenzene or hexamethylbenzene or a mixture of both.

18 Claims, No Drawings

PREPARATION OF POLYMETHYLBENZENES

BACKGROUND OF THE INVENTION

This invention relates to a process for preparing polymethylbenzenes, particularly pentamethylbenzene and hexamethylbenzene. In another aspect, this invention relates to a process for preparing polymethylbenzenes by reaction of a phenolic compound and a methyl compound. In a still further aspect, this invention relates to a catalytic process for preparing polymethylbenzenes. In still another aspect, this invention relates to a process for making hexamethylbenzene, which is useful as an intermediate in the fragrance industry.

Processes for preparing polymethylbenzenes are known, such as the processes for preparing hexamethylbenzene in the presence of a Friedel-Crafts catalysts, as described in U.S. Pat. No. 3,869,524. However, there is an ever present need to develop new processes for preparing polymethylbenzenes, especially processes employing simpler, less sensitive catalyst systems than those previously known and different reactants.

SUMMARY OF THE INVENTION

It is an object of this invention to provide a process for making polymethylbenzenes. It is another object of this invention to provide a process for preparing either pentamethylbenzene or hexamethylbenzene or a mixture of both. It is a further object of this invention to prepare polymethylbenzenes in a process utilizing a spinell-type catalyst. It is a still further object of this invention to prepare polymethylbenzenes by methylation of a phenolic compound.

In accordance with this invention, at least one polymethylbenzene selected from the group consisting of pentamethylbenzene and hexamethylbenzene is prepared by contacting under suitable reaction conditions (a) at least one phenolic compound selected from the group consisting of phenol, methylphenols, dimethylphenols, trimethylphenols and tetramethylphenols; with (b) methanol or a methyl alkyl ether; in the presence of (c) a catalyst composition comprising zinc aluminate. The presently preferred phenolic compound is phenol. The preferred methylating compound is methanol. In one embodiment the reaction mixture of (a) and (b) and the catalyst composition in contact therewith are at an elevated temperature.

DETAILED DESCRIPTION OF THE INVENTION

A process is provided for preparing at least one polymethylbenzene by contacting simultaneously:
(a) a first reactant comprising at least one phenolic compound selected from the group consisting of phenol, methylphenols, dimethylphenols, trimethylphenols and tetramethylphenols; with
(b) a second reactant comprising at least one methyl compound (methylating agent) selected from the group consisting of methanol and methyl alkyl ethers; in the presence of
(c) a catalyst composition comprising zinc aluminate; under such reaction conditions as will result in the at least partial conversion of (a) and (b) to at least one compound selected from the group consisting of pentamethylbenzene and hexamethylbenzene.

Examples of methylphenols are o-, m- and p-methylphenol. Examples of dimethylphenols are 2,4-dimethylphenol, 2,6-dimethylphenol, 3,5-dimethylphenol. Non-limiting examples of trimethylphenols are 2,4,6-trimethylphenol, 2,3,4-trimethylphenol and 3,4,5-trimethylphenol. Non-limiting examples of tetramethylphenols are 2,3,4,5-tetramethylphenol and 2,3,4,6-tetramethylphenol. The preferred phenolic reactant is phenol, primarily because of its availability and low cost.

Methyl alkyl ethers, $CH_3-O-R$, that are useful, yet less preferred, as methylating agents in this invention have an alkyl group R containing from 1 to 6 C-atoms per group. Non-limiting examples of methyl alkyl ethers are: dimethyl ether, methyl ethyl ether, methyl n-propyl ether, methyl tert-butyl ether, methyl n-hexyl ether and the like.

Methanol is the preferred reactant (b). It can be used as a "neat" $CH_3OH$ liquid or vapor or as a mixture containing reagents that will form methanol in-situ, e.g., a mixture of methyl halide and water.

The catalyst composition containing zinc aluminate can be prepared by any means known in the art, e.g., by coprecipitation of zinc oxide or zinc hydroxide and aluminum oxide or aluminum hydroxide plus subsequent calcination; or by impregnation of alumina with a solution of a zinc salt, such as zinc nitrate, plus subsequent calcination; or by mixing and fusing dry powders of $Al_2O_3$ and ZnO; or by mixing aqueous or non-aqueous slurries or pastes of zinc oxide and aluminum oxide plus subsequent calcining, and the like. U.S. Pat. Nos. 3,641,182 and 3,674,706; herein incorporated by reference, disclose suitable methods of preparing zinc aluminate. The presently preferred method of preparing zinc aluminate, particularly $ZnAl_2O_4$, is disclosed in U.S. Pat. No. 3,674,706 column 3, lines 6–16, and comprises ball-milling of slurried ZnO and $Al_2O_3$ and subsequent calcining. Generally, the mole ratio of ZnO to $Al_2O_3$ in the preparation of the zinc aluminate-containing catalyst compositions of this invention ranges from about 1:0.7 to about 1:1.3, and is preferably about 1:1. Preferably, the surface area of the zinc aluminate containing catalyst composition ranges from about 20 to 30 $m^2/g$ (determined by the $BET/N_2$ method), and its pore volume ranges from about 0.25 to about 0.40 mL/g (as determined by mercury porosimetry at a pressure of 15 Kpsi Hg).

The zinc aluminate-containing catalyst composition can be used as powder or, preferably, in pelletized form. In addition, the zinc aluminate-containing catalyst composition can be admixed with other refractory oxides such as silica, magnesia, thoria; $AlPO_4$, alumino-silicates and the like. Also, the zinc aluminate containing catalyst composition can also contain small amounts (e.g., up to 5 weight-%) of metals of Groups IIA, IVA, IVB, VB, VIB, VIIB, VIII and IB, or compounds thereof.

The intimate contacting of at least one phenolic compound, at least one methyl compound and the zinc aluminate-containing catalyst composition can be carried out in any suitable reactor, either in a batch process or in a continuous process. The three above-cited process ingredients can be added essentially simultaneously or sequentially in any order to a reactor, or they can be added in premixed form, and the resulting slurry can then be agitated. Or the phenolic compound and the methyl compound, preferably premixed, can be passed through a reactor comprising the zinc aluminate containing catalyst composition as a fixed bed. Premixing can be carried out in a separate vessel having agitating or static mixing means. It is also within the scope of this invention to employ a moving catalyst bed or an ebulliating catalyst bed operation. Presently preferred is a fixed catalyst bed operation.

Optionally, the phenolic compound and the methyl compound can be dissolved in a suitable inert solvent, which is capable of also solubilizing the reaction product(s) (penta- and/or hexamethyl benzene). The solvent is present during at least part of the time of contacting the phenolic and methyl compounds in the presence of the zinc aluminate catalyst under suitable reaction conditions. Suitable solvents are normally liquid (i.e., liquid at room temperature and about 1 atm) paraffins, cycloparaffins, and aromatic hydrocarbons, each preferably containing from 5 to 11 carbon atoms per molecule such as n-pentane iso-pentanes, n-hexane, iso-hexanes, n-decane, iso-decanes, undecanes, cyclohexane, methylcyclohexane, benzene, toluene, xylenes and the like. The presently preferred solvent is toluene.

Generally the methylating agent is employed at an excess of at least 10% over what is required stoichiometrically. If methanol is used, the mole ratio of methanol to the phenolic compound generally ranges from about 2:1 to about 20:1, depending on the phenolic compound used. If the phenolic compound is phenol, the mole ratio of methanol to phenol preferably ranges from about 6:1 to about 15:1. If a solvent is present, it can be present at a weight ratio of solvent to (methyl compound plus phenolic compound) ranging from about 0.1:1 to about 10:1, preferably from about 0.3:1 to about 1:1.

The liquid hourly space velocity (LHSV), i.e., the ratio of the combined volume of methanol and phenolic compound to the volume of the catalyst composition per hour of intimate contact at reaction conditions, generally ranges from about 0.1 to about 10 cc/cc/hr, preferably from about 0.3 to about 2 cc/cc/hr. In the preferred continuous fixed catalyst bed operation, the above-recited LHSV is attained by adjusting the feed rates of methanol plus phenolic compound. In a batch-type operation, a total reaction time is selected such as to give the above-recited volume ratio per hour of intimate contact time.

Any reaction temperature that will initiate and maintain a controllable reaction can be employed. The reaction temperature generally ranges from about 220° C. to about 600° C., preferably from about 265° C. to about 440° C. The reaction pressure is not considered critical and can be atmospheric (i.e., about 1 atm), subatmospheric or superatmospheric. The selection of the reaction pressure will greatly depend on the reaction temperature, on the volatility of the reactants, solvent (if used) and formed reaction products, and on the reactor design. Any suitable heating and pressuring means can be employed. It is also within the scope of this invention to preheat the phenolic compound and methanol before their introduction into the reactor.

The formed reaction products, pentamethylbenzene and/or hexamethylbenzene, can be separated from the reaction mixture by any suitable separation means such as fractional distillation, crystallization, extraction with a suitable solvent plus subsequent evaporation of the solvent and the like, preferably by crystallization. Unreacted process ingredients can be separated in a similar manner and can be recycled to the reaction zone with fresh reactants. The formed products can be purified by washing, recrystallization and chromatographic methods. The separation of the reaction products into pentamethylbenzene and hexamethylbenzene, if both are formed, can be accomplished by fractional crystallization. Hexamethylbenzene is a valuable chemical intermediate used in the production of perfumery materials.

The following examples are presented to further illustrate this invention without unduly limiting the scope of this invention.

EXAMPLE I

This example describes the general procedure used for evaluating the catalyst described herein for the methylation of phenol. To a 1 inch I.D. ×2 foot stainless steel vertical pipe reactor equipped with inlet and outlet adaptor, pressure regulator, thermocouples and external heaters were charged about 150 to 200 milliliters of catalyst pellets. The column was heated (top: about 400° C.; bottom: about 320° to 370° C.) while a solution of 133 grams (1.4 moles) phenol, 600 grams (18.8 moles) methyl alcohol, and 400 grams cyclohexane was pumped through the reactor at a rate of 1 to 2 milliliters per minute (LHSV 0.3 to 0.8 volumes of feed/volume of catalyst/hour) at an internal reactor pressure of about 500 psig.

The run was continued for 6 to 8 hours while the effluent was periodically analyzed by gas-liquid chromatography (GLC) using a 10 meter capillary column with a silicone OV101 surface coating, a flame detector programmed from 75° C. to 250° C. at 10° C./minute and a He flow of 60 cubic centimeters/minute. The effluent was collected whereby both hexamethylbenzene and pentamethylbenzene crystallized upon cooling and were removed by filtration. These products could be separated by fractional crystallization.

Table I shows the results of runs using three different catalysts. These results indicate that preferred catalyst, zinc aluminate, gives a higher selectivity of the desired products pentamethylbenzene and hexamethylbenzene than the aluminum oxide catalyst tested. In addition, the zinc aluminate catalyst gave very few substituted phenols, as did the aluminum oxide catalyst.

TABLE I

|  | Run 1 (Control) | Run 2 (Control) | Run 3 (Invention) |
| --- | --- | --- | --- |
| Catalyst | $Al_2O_3$[a] | $Al_2O_3$[a] | Zn Aluminate[b] |
| T° C. | 300–370 | 350–370 | 330–360 |
| Moles MeOH: Phenol | 13 | 10 | 10 |
| Solvent | cyclohexane | toluene | toluene |
| LHSV, Feed Vol/ hr ÷ Cat. Vol. | 0.3–0.4 | 0.3–0.4 | 0.3–0.4 |
| % Conversion of Phenol | 100 | 100 | 100 |
| % Selectivity to |  |  |  |
| Cresols | <1 | <1 | ↑ |
| Dimethylphenols | 3–4 | 7–8 |  |
| Trimethylphenols | 9 | 10–12 | nil |
| Tetramethylphenols | 6 | 8–9 |  |
| Pentamethylphenol | 14 | 16–17 | ↓ |
| Pentamethylbenzene | 13 | 6–7 | 35–25 |
| Hexamethylbenzene | 48 | 35–45 | 65–75 |

[a]Gamma alumina from Strem Chem. Co., Newbury Port, Massachusetts.
[b]$ZnAl_2O_4$ having a surface area of 20–30 $m^2$/g, a pore volume of 0.25–0.50 mL/g; prepared substantially in accordance with the procedure described in U.S. Pat. No. 3,674,706 column 3, lines 6–16.

EXAMPLE II

This example, illustrates the effects of various process parameters on the conversion of phenol plus methanol to penta- and hexamethylbenzene over zinc aluminate as catalyst. The experimental setup was essentially the same as described in Example I. Test results are summarized in Table II.

TABLE II

| Temp., °C. | Feed LHSV[a] | Weight % Toluene[b] | Methanol: Phenol Mol Ratio | % Convers. of Phenol | % Selectiv. to PMB[c] | % Selectiv. to HMB[d] |
| --- | --- | --- | --- | --- | --- | --- |
| 320 | 1 | 49 | 1.8 | 90 | 2 | 1 |
| 340 | 1 | 67 | 5.7 | 100 | 24 | 33 |
| 320 | 1 | 28 | 9.5 | 100 | 18 | 32 |
| 360 | 1 | 52 | 13.3 | 100 | 30 | 67 |
| 320 | 1 | 28 | 9.5 | 100 | 18 | 32 |
| 280 | 1 | 44 | 9.5 | 90 | 25 | 51 |
| 300 | 1 | 72 | 9.5 | 100 | 22 | 70 |
| 370 | 0.3 | 52 | 13.3 | 100 | 48 | 46 |
| 360 | 0.5 | 52 | 13.3 | 100 | 41 | 56 |
| 360 | 1 | 52 | 13.3 | 100 | 30 | 67 |
| 200 | 0.5 | 28 | 9.5 | <50 | — | — |
| 250 | 0.5 | 28 | 9.5 | 100 | 10 | 7 |
| 250 | 1 | 28 | 9.5 | 88 | — | 6 |
| 360 | 0.5 | 67 | 5.7 | 100 | 29 | 26 |
| 340 | 1 | 67 | 5.7 | 100 | 24 | 33 |
| 360 | 1.5 | 67 | 5.7 | 100 | 15 | 20 |
| 200 | 0.5 | 28 | 9.5 | <50 | — | — |
| 250 | 1 | 28 | 9.5 | 88 | — | 6 |
| 280 | 1 | 44 | 9.5 | 90 | 25 | 51 |
| 300 | 1 | 72 | 9.5 | 100 | 22 | 65 |
| 350 | 1 | 72 | 9.5 | 100 | 26 | 67 |
| 360[e] | 1 | 72 | 9.5 | 100 | 33 | 64 |
| 400 | 1 | 72 | 9.5 | 100 | 37 | 58 |
| 440 | 1 | 72 | 9.5 | 100 | 46 | 8 |

[a] Volume of (methanol plus phenol) per hour per volume of catalyst
[b] used as solvent
[c] pentamethylbenzene
[d] hexamethylbenzene Data in Table II show that the reaction temperature and the methanol:phenol ratio had the most significant effects on the phenol conversion and on the selectivity to penta- and hexamethylbenzene. A reaction temperature of at least about 250°–280° C. and a methanol:phenol mole ratio of at least about 5:1 were preferred so as to achieve highest yields of pentamethylbenzene and/or hexamethylbenzene.

Reasonable variations and modifications can be made in this invention without departing from the spirit and scope thereof.

I claim:

1. A process for preparing at least one polymethylbenzene comprising the step of (A) contacting simultaneously:
   (a) a first reactant comprising at least one phenolic compound selected from the group consisting of phenol, methylphenols, dimethylphenols, trimethylphenols and tetramethylphenols; with
   (b) a second reactant comprising at least one methyl compound selected from the group consisting of methanol and methyl alkyl ethers, wherein the alkyl group contains from 1 to 6 carbon atoms per group; in the presence of
   (c) a catalyst composition comprising zinc aluminate; under such reaction conditions as will result in the at least partial conversion of (a) and (b) to at least one compound selected from the group consisting of pentamethylbenzene and hexamethylbenzene.

2. A process in accordance with claim 1 wherein the methyl compound is methanol.

3. A process in accordance with claim 2 wherein the phenolic compound is phenol.

4. A process in accordance with claim 3 wherein said reaction conditions comprise a reaction temperature ranging from about 220° C. to about 600° C.

5. A process in accordance with claim 2 wherein the mole ratio of methanol to phenolic compounds ranges from about 2:1 to about 20:1.

6. A process in accordance with claim 3 wherein the reaction temperature ranges from about 265° C. to about 440° C. and the mole ratio of methanol to phenol ranges from about 6:1 to about 15:1.

7. A process in accordance with claim 1 wherein an inert solvent is present during at least part of the time of said contacting, said inert solvent being selected from the group consisting of normally liquid paraffins, cycloparaffins and aromatic hydrocarbons having from 5 to 11 carbon atoms per molecule.

8. A process in accordance with claim 3 wherein an inert solvent is present during at least part of the time of said contacting, said inert solvent being selected from the group consisting of normally liquid paraffins, cycloparaffins and aromatic hydrocarbons having from 5 to 11 carbon atoms per molecule.

9. A process in accordance with claim 8 wherein the inert solvent is toluene.

10. A process in accordance with claim 9 wherein the weight ratio of toluene to (methanol plus phenol) ranges from about 0.1:1 to about 10:1.

11. A process in accordance with claim 9 wherein the weight ratio of toluene to (methanol plus phenol) ranges from about 0.3:1 to about 1:1.

12. A process in accordance with claim 10 wherein the reaction temperature ranges from about 265° C. to about 440° C. and the mole ratio of methanol to phenol ranges from about 6:1 to about 15:1.

13. A process in accordance with claim 11, wherein the reaction temperature ranges from about 265° C. to about 440° C. and the mole ratio of methanol to phenol ranges from about 6:1 to about 15:1.

14. A process in accordance with claim 1 wherein the chemical formula of zinc aluminate is $ZnAl_2O_4$.

15. A process in accordance with the process of claim 14 wherein the surface area of zinc aluminate ranges from about 20 to about 30 $m^2/g$ (as determined by the BET/$N_2$ method).

16. A process in accordance with claim 1 comprising the additional step (B) of separating the reaction products comprising at least one compound selected from the group consisting of pentamethylbenzene and hexamethylbenzene from the reaction mixture.

17. A process in accordance with claim 16 wherein the reaction products are separated from the reaction mixture by crystallization.

18. A process in accordance with claim 16, wherein the reaction products comprise a mixture of pentamethylbenzene and hexamethylbenzene, comprising the further step (C) of separating the reaction products into pentamethylbenzene and hexamethylbenzene by fractional crystallization.

* * * * *